(12) United States Patent
Maeda et al.

(10) Patent No.: US 6,639,084 B2
(45) Date of Patent: Oct. 28, 2003

(54) CHEMICALLY AMPLIFIED RESIST, POLYMER FOR THE CHEMICALLY AMPLIFIED RESIST, MONOMER FOR THE POLYMER AND METHOD FOR TRANSFERRING PATTERN TO CHEMICALLY AMPLIFIED RESIST LAYER

(75) Inventors: Katsumi Maeda, Tokyo (JP); Kaichiro Nakano, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 10/167,499

(22) Filed: Jun. 13, 2002

(65) Prior Publication Data

US 2003/0097008 A1 May 22, 2003

(30) Foreign Application Priority Data

Jun. 15, 2001 (JP) .................................... 2001-181716
Dec. 26, 2001 (JP) .................................... 2001-394173

(51) Int. Cl.$^7$ ............................................ C07D 313/16
(52) U.S. Cl. .................. 549/266; 430/270.1; 338/15; 252/511
(58) Field of Search ................ 549/266, 283; 338/15; 252/511; 430/270.1

(56) References Cited

FOREIGN PATENT DOCUMENTS

| JP | 2-27660 A | 1/1990 |
|---|---|---|
| JP | 5-134416 A | 5/1993 |
| JP | 2000-26446 A | 1/2000 |
| JP | 2001-188351 A | 7/2001 |

OTHER PUBLICATIONS

S. Takechi et al., "Alicyclic Polymer for ArF and KrF Excimer Resist Based on Chemical Amplification", Journal of Photopolymer Science and Technology, vol. 5, No. 3, (1992), pp. 439–446.

R. D. Allen et al., "Resolution and Etch Resistance of a Family of 193 nm Positive Resists", Journal of Photopolymer Science and Technology, vol. 8, No. 4, (1995), pp. 623–636.

R. D. Allen et al., "Progress in 193 nm Positive Resists", Journal of Photopolymer Science and Technology, vol. 9, No. 3, (1996), pp. 465–474.

F. M. Houlihan et al., "Synthesis of Cycloolefin–Maleic Anhydride Alternating Copolymers for 193 nm Imaging", Macromolecules, vol. 30, No. 21, (1997), pp. 6517–6524.

J. V. Criello et al., "A New Preparation of Triaylsulfonium and —selenonium Salts via the Copper (II)—Catalyzed Arylation of Sulfides and Selenides with Diaryiiodonium Salts", J. Org. Chem., vol. 43, No. 15, (1978), pp. 3055–3058.

J. P. Mathew et al., "($\eta^3$Allyl)palladium (II) and Palladium (II) Nitrile Catalysts for the Addition Polymerization of Norbornene Derivatives with Functional Groups", Macromolecules, 29kann, pp. 2755–2763 with Abstract 1996.

T. Chiba et al., "157 nm Resist Materials: A Progress Report", Journal of Photopolymer Science and Technology, vol. 13, No. 4, (2000), pp. 657–664.

D. C. Hofer et al., "193 nm Photoresist R&D: The Risk & Challenge", Journal of Photopolymer Science and Technology, vol. 9, No. 3, (1996), pp. 387–397.

"Chemical Handbook basic II", revised edition 3, editited by Japanese Chemical Society and published by Maruzen Corporation, pp. 502–504 (1984).

F. M. Houlihan et al., "The Synthesis, Characterization and Lithography of α–Substituted 2–Nitrobenzyl Arylsulfonate Photo–Acid Generators with Improved Resistance to Post Exposure Bake", SPIE, vol. 2195, pp. 137–151. (1994).

T. Ueno et al., "Chemical Amplification Positive Resist Systems Using Novel Sulfonates as Acid Generators", Proceedings of PME' 89, Kohdansha, pp. 413–424 with Abstract (1990).

*Primary Examiner*—Taofiq Solola
(74) *Attorney, Agent, or Firm*—Sughrue Mion, LLP

(57) ABSTRACT

Chemically amplified resist is produced on the basis of vinyl polymer having 3-oxo-4-oxabicyclo[3.2.1]otane-2-yl group expressed by general formula (1)

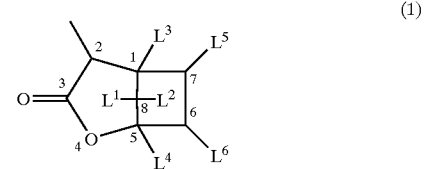

(1)

where each of $L^1$, $L^2$, $L^3$, $L^4$, $L^5$ and $L^6$ is selected from the group consisting of hydrogen atom and alkyl groups having the carbon number from 1 to 8, and the hydrogen atom and/or the alkyl group at $L^5$ and $L^6$ are replaced with alkylene groups having the carbon number from 1 to 10 and bonded to each other for forming a ring so that the resist exhibits high transparency to light equal to or less than 220 nm wavelength, large resistance against dry etching and good adhesion to substrates.

9 Claims, No Drawings

CHEMICALLY AMPLIFIED RESIST, POLYMER FOR THE CHEMICALLY AMPLIFIED RESIST, MONOMER FOR THE POLYMER AND METHOD FOR TRANSFERRING PATTERN TO CHEMICALLY AMPLIFIED RESIST LAYER

FIELD OF THE INVENTION

This invention relates to compounds used in photoresist and, more particularly, to chemically amplified photoresist sensitive to far-ultraviolet light equal in wavelength to or less than 220 nanometers, polymer used for producing the chemically amplified resist, monomer for producing the polymer and a method for transferring a pattern to a chemically amplified resist layer.

DESCRIPTION OF THE RELATED ART

Pattern images are sequentially transferred to semiconductor wafers in processes for fabricating semiconductor devices, and design rules have been renewed in the fabrication process. Now, semiconductor devices are designed under sub-micron rules, and requirements for the photolithography get sever and sever.

Manufacturers require 0.13 micron patterns for 1 giga-bit DRAMs (Dynamic Random Access Memory), and research and development efforts are being made for the photolithography used in the ultra large scale integration. 193-nanometer wavelength ArF excimer laser lithography is disclosed by Donald C. Hofer et. al. in "193 nm Photoresist R & D: The Risk & Challenge", Journal of Photopolymer Science and Technology, vol. 9, No. 3, pages 387–397, 1996. The ArF excimer laser lithography requires new photoresist. The ArF excimer laser system is expensive, and the gaseous mixture used therein is short in-lifetime. In these circumstances, the new photoresist is expected to be highly sensitive to the ArF excimer laser light as well as the high resolution from the viewpoint of the cost performance.

The chemically amplified photoresist is attractive. The chemically amplified photoresist contains photo-acid generator, which accelerates the chemical reaction in the photoresist. A typical example of the chemically amplified photoresist is disclosed in Japanese Patent Application laid-open No. 2-27660. The prior art chemically amplified photoresist contains triphenylsulfonium hexafluoroarsenate and poly (p-tert-butoxycarbonyloxy-a-methylstyrene). The prior art chemically amplified photoresist is presently used in KrF excimer laser lithography as taught by Hiroshi Itoh and C. Grantwillson, American Chemical Society Symposium Series, vol. 242, pages 11–23, 1984.

When the chemically amplified photoresist is exposed to the light, proton acid is generated from the photo-acid generator. The proton acid reacts with the copolymer in the heat treatment after the exposure to the light. The amount of reaction per photon, i.e., photoreaction efficiency is enhanced through the acid-catalyzed reaction. Although the photoreaction efficiency is less than 1 in the conventional photoresist, the chemically amplified photoresist achieves the photoreaction efficiency greater than 1, and most of new products of photoresist presently developed are of the type chemically amplified.

The ArF excimer laser is an example of the short-wavelength band equal to or less than 220 nanometers. The photoresist available for the photolithography in the short-wavelength band is expected to be transparent to the exposure light and large in resistance against dry etching. The prior art products of photoresist, which are responsive to g-line with 438 nanometer wavelength, i-line with 365 nanometer wavelength or KrF excimer laser light with 248 nanometer wavelength, contain copolymer having the structural unit with the aromatic ring such as novolak resin or poly (p-vinylphenol), and the aromatic ring makes the copolymer resistive against the dry etching.

Although the copolymer with the aromatic ring is preferable for the KrF excimer laser light or the long wavelength rays, the copolymer exhibits strong light absorption to the light in the short wavelength band equal to or greater than 220 nanometer wavelength. In fact, when the prior art photoresist based on the copolymer is exposed,to the ArF excimer laser light, most of the ArF excimer laser light is absorbed in the surface portion of the prior art photoresist layer, and hardly reaches the substrate. This means that any fine pattern is not obtained from the prior art photoresist layer.

As described hereinbefore, the prior art products of photoresist are not available for the ArF excimer laser lithography, and the semiconductor manufacturers desire a new product of photoresist available for the ArF excimer laser lithography. The structural unit of the photoresist is expected to exhibit large resistance against dry etching without the aromatic ring, because the photoresist would exhibit the transparency to the ArF excimer laser light.

The prior art photoresist available for 193 nm ArF excimer laser lithography is taught by Takechi et. al., Journal of Photopolymer Science and Technology, vol. 5, No. 3, pages 439 to 446, 1992. The photoresist is based on copolymer having adamantyl methacrylate units which are alicyclic polymer. Another prior art photoresist is based on copolymer having isobornyl methacrylate units as disclosed by R. D. Allen et. al, Journal of Photopolymer Science and Technology, vol. 8, No. 4, pages 623 to 636, 1995 and vol. 9, No. 3, pages 465–474, 1996. Yet another prior art photoresist is based on copolymer having the structural unit of alternating copolymerization between norbornene and maleic anhidride as taught by F. M. Houlihan et. al, Macromolecules, vol. 30, pages 6517–6524, 1997.

Carboxy group and hydroxy group are categorized in the polar groups. The polar group makes the photoresist strongly held in contact with substrates, and are preferable to the photoresist. However, the aforementioned monomer, which has the alicyclic group, does not have any polar group. The prior art photoresist is hydrophobic, and the photoresist layer is liable to peel off from the substrates such as silicon substrates. Thus, the first drawback inherent in the prior art photoresist is the weak adhesion to substrates.

The second drawback inherent in the photoresist containing the polymer having an alicyclic group is poor uniformity of film formation. When the prior art photoresist is spread over substrates, the prior art photoresist layers are irregular in thickness. This phenomenon is also derived from the hydrophobic property due to the lack of the polar group.

The third drawback is a small difference in solubility between the pre-exposure to light and the post-exposure. Adamantyl—containing residue, isobornyl—containing residue and menthyl—containing residue give the strong resistance against dry etching to the photoresist. However, the prior art photoresist does not have any residue which makes the photoresist widely different in solubility between the pre-exposure to light and the post-exposure. This means that the photoresist layer has a dull edge.

It is possible to overcome those drawbacks by employing copolymerization with certain comonomers for improving the difference in solubility and/or comonomers for enhancing the adhesion to substrates. t-butyl methacrylate and tetrahydropyranyl methacrylate are examples of the comonomer for improving the difference in solubility, and methacrylic acid is an example of the comonomer for enhancing the adhesion to substrates. However, the comonomer is required at least 50 mole %. The comonomer is less resistive against dry etching. Thus, the manufacturers desire new photoresist which exhibits high transparency to the exposure light, large difference in the solubility and strong adhesion to substrates without sacrifice of the resistance against dry etching.

The other sorts of photoresist, which contain the alternating copolymerization between norbornene and maleic anhydride, have the norbornane ring. The norbornane ring also does not have any polar group, and the photoresist exhibits poor adhesion. When copolymer with acrylic acid is introduced into the resin based on the alternating copolymer between norbornene and maleic anhydride, the adhesion is improved. However, the resultant photoresist is less resistive against dry etching. The manufacturers also desire new photoresist exhibiting strong adhesion to substrates without sacrifice of the resistance against dry etching.

SUMMARY OF THE INVENTION

It is therefore an important object of the present invention to provide photoresist which exhibits high transparency to light equal in wavelength to or less than 220 nm, large resistance against dry etching and strong adhesion to substrates.

It is another important object of the present invention to provide polymer to be used in the photoresist.

It is yet another important object of the present invention to provide monomer to be used in the polymer.

It is still another important object of the present invention to provide a method for transferring a pattern to the photoresist layer.

The present inventors found that 3-oxo-4-oxabicyclo [3.2.1]otane-2-yl skeleton was useful for photoresist. The present inventors examined documents referring to photoresist having the skeleton. Japanese Patent Application laid-open No. 2001–188351 taught the photoresist having the bridged alicyclic skeleton in which at least one ring is lactone ring. Norbornyl monoene, norbornyl diene, tricyclodecamonoene, tricyclodecadiene, tetracyclodecamonoene and tetracyclodecadiene were written in the Japanese Patent Application laid-open as the examples. Japanese Patent Application laid-open No. 2000–26446 taught (meth) acrylate polymer having the bridged lactone structure. However, the present inventors could not find any document teaching that 3-oxo-4-oxabicyclo[3.2.1]otane-2-yl skeleton was useful for phoioresist.

In accordance with one aspect of the present invention, there is provided monomer for a chemically amplified photoresist comprising vinyl monomer having 3-oxo-4-oxabicyclo[3.2.1]otane-2-yl group expressed by general formula (1)

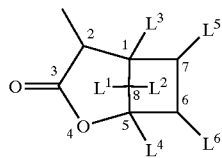

where each of $L^1$, $L^2$, $L^3$, $L^4$, $L^5$ and $L^6$ is selected from the group consisting of hydrogen atom and alkyl groups having the carbon number from 1 to 8.

The hydrogen atom or alkyl group at $L^5$ and the hydrogen atom or alkyl group at $L^6$ may be replaced with alkylene groups having the carbon number 1 to 10 and bonded to each other for forming a ring.

The 3-oxo-4-oxabicyclo[3.2.1]otane-2-yl group expressed by general formula (1) may be replaced with vinyl monomer with a bridged alicylic δ lactone structure expressed by general formula (2)

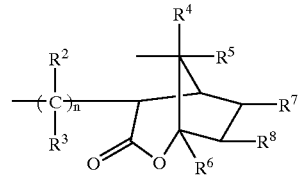

where each of $R^2$ and $R^3$ is selected from the group consisting of hydrogen and alkyl groups having the carbon number from 1 to 4, each of $R^4$ to $R^6$ is selected from the group consisting of hydrogen atom and methyl group, $R^7$ and $R^8$ are hydrogen atoms or alkylene groups each having the carbon number from 1 to 10 and bonded for forming a ring and n is zero or 1.

In accordance with another aspect of the present invention, there is provided polymer used for a chemically amplified photoresist comprising vinyl polymer having 3-oxo-4-oxabicyclo[3.2.1]otane-$^2$-yl group expressed by general formula (1)

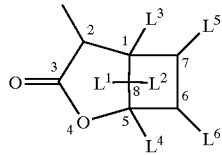

where each of $L^1$, $L^2$, $L^3$, $L^4$, $L^5$ and $L^6$ is selected from the group consisting of hydrogen atom and alkyl groups having the carbon number from 1 to 8.

The hydrogen atom or alkyl group at $L^5$ and the hydrogen atom or alkyl group at $L^6$ may be replaced with alkylene groups having the carbon number 1 to 10 and bonded to each other for forming a ring.

The 3-oxo-4-oxabicyclo[3.2.1]otane-2-yl group expressed by general formula (1) may be replaced with vinyl monomer with a bridged alicylic δ lactone structure expressed by general formula (2)

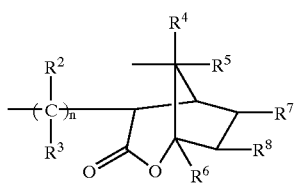

(2)

where each of $R^2$ and $R^3$ is selected from the group consisting of hydrogen and alkyl groups having the carbon number from 1 to 4, each of $R^4$ to $R^6$ is selected from the group consisting of hydrogen atom and methyl group, $R^7$ and $R^8$ are hydrogen atoms or alkylene groups each having the carbon number from 1 to 10 and bonded for forming a ring and n is zero or 1.

In accordance with yet another aspect of the present invention, there is provided photoresist comprising polymer including vinyl polymer having 3-oxo-4-oxabicyclo[3.2.1]otane-2-yl group expressed by general formula (1)

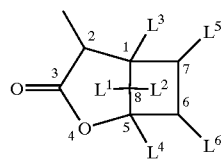

(1)

where each of $L^1$, $L^2$, $L^3$, $L^4$, $L^5$ and $L^6$ is selected from the group consisting of hydrogen atom and alkyl groups having the carbon number from 1 to 8, and photo-acid generator generating acid in the presence of light equal in wavelength to or less than 220 nanometers; the ratio of the photo-acid generator to the photoresist is fallen within the range from 0.2% by mass to 30% by mass.

The hydrogen atom or alkyl group at $L^5$ and the hydrogen atom or alkyl group at $L^6$ may be replaced with alkylene groups having the carbon number 1 to 10 and bonded to each other for forming a ring.

The 3-oxo-4-oxabicyclo[3.2.1]otane-2-yl group expressed by general formula (1) may be replaced with vinyl monomer with a bridged alicylic δ lactone structure expressed by general formula (2)

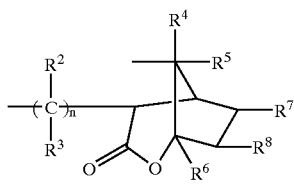

(2)

where each of $R^2$ and $R^3$ is selected from the group consisting of hydrogen and alkyl groups having the carbon number from 1 to 4, each of $R^4$ to $R^6$ is selected from the group consisting of hydrogen atom and methyl group, $R^7$ and $R^8$ are hydrogen atoms or alkylene groups each having the carbon number from 1 to 10 and bonded for forming a ring and n is zero or 1.

In accordance with still another aspect of the present invention, there is provided a method for transferring a pattern to a photoresist layer, comprising the steps of a) preparing a substrate and photoresist comprising polymer including polymer having 3-oxo-4-oxabicyclo[3.2.1]otane-2-yl group expressed by general formula (1)

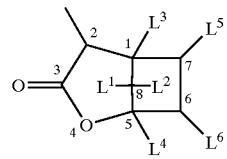

(1)

where each of $L^1$, $L^2$, $L^3$, $L^4$, $L^5$ and $L^6$ is selected from the group consisting of hydrogen atom and alkyl groups having the carbon number from 1 to 8 and photo-acid generator generating acid in the presence of light equal in wavelength to or less than 220 nanometers, the ratio of the photo-acid generator to the photoresist being fallen within the range from 0.2% by mass to 30% by mass, b) spreading the photoresist on the substrate for forming a photoresist layer, c) exposing the photoresist layer to image-carrying light having a wavelength between 180 nanometers and 220 nanometers for forming a latent image in the photoresist layer, and d) developing the latent image so as to pattern the photoresist layer into a photoresist patterned layer.

The hydrogen atom or alkyl group at $L^5$ and the hydrogen atom or alkyl group at $L^6$ may be replaced with alkylene groups having the carbon number 1 to 10 and bonded to each other for forming a ring.

The 3-oxo-4-oxabicyclo[3.2.1]otane-2-yl group expressed by general formula (1) may be replaced with vinyl monomer with a bridged alicylic δ lactone structure expressed by general formula (2)

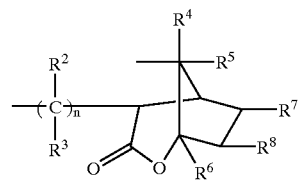

(2)

where each of $R^2$ and $R^3$ is selected from the group consisting of hydrogen and alkyl groups having the carbon number from 1 to 4, each of $R^4$ to $R^6$ is selected from the group consisting of hydrogen atom and methyl group, $R^7$ and $R^8$ are hydrogen atoms or alkylene groups each having the carbon number from 1 to 10 and bonded for forming a ring and n is zero or 1

The present inventors selected the 3-oxo-4-oxabicyclo [3.2.1]otane-2-yl skeleton from the bridged alicylic δ lactone skeletons for the polymer used for chemically amplified photoresist according to the present invention. The 3-oxo-4-oxabicyclo[3.2.1]otane-2-yl skeleton enhanced the transparency of the chemically amplified photoresist to the light equal in wavelength to or less than 220 nanometers without sacrifice of the resistance against etching and adhesion to substrates. The reasons for the preferable features were as follows.

First, the present inventors discovered that bicyclo[3.2.1] otane skeleton made the photoresist transparent to the light equal in wavelength to or less than 220 nanometers and resistive to dry etching. The reason for the high transparency was that the bridged alicylic structure did not have any aromatic ring. The carbon density was so high that the bridged alicylic structure well withstood the dry etching. Especially, the bicyclo[3.2.1]otane had the molecular structure desirable from the viewpoint of the transparency and the resistance against dry etching. The 3-oxo-4-oxabicyclo [3.2.1]otane-2-yl skeleton included the bicyclo[3.2.1.]otane skeleton so that the photoresist according to the present invention exhibited high transparency without sacrifice of the resistance against the dry etching.

Second, δ lactone ring had the dielectric constant larger in value than that of the ester structure, ether structure and alcohol structure. Referring to "CHEMICAL HANDBOOK basic II", revised edition 3, pages 502 to 504, edited by Japanese Chemical Society and published by Maruzen Corporation, the dielectric constant of the compounds having the carbon number 4 were as follows. The dielectric constant of γ-buthyrolactone was 39, the dielectric constant of ethyl accetate was 6.02, the dielectric constant of diethyl ether was 4.535, and the dielectric constant of 1-butanol was 17.51. Thus, the lactone structure was larger in dielectric constant than the other structures. The large dielectric constant resulted in clear polarity. Especially, the δ lactone exhibited an appropriate value of the dielectric constant. The large dieelctric constant was desirable for adhesion to substrates. The 3-oxo-4-oxabicyclo[3.2.1]otane-2-yl skeleton had the δ lactone ring so that the photoresist according to the present invention achieved strong adhesion to substrates.

The 3-oxo-4-oxabicyclo[3.2.1]otane-2-yl skeleton had both of the bicyclo[3.2.1]otane skeleton and the δ lactone skeleton. This meant that the 3-oxo-4-oxabicyclo[3.2.1] otane-2-yl skeleton was expected to exhibit synergism of the bicyclo[3.2.1]otane skeleton and the δ lactone skeleton. Thus, the 3-oxo-4-oxabicyclo[3.2.1]otane-2-yl skeleton was desirable for the transparency to the light, resistance against dry etching and strong adhesion to substrates.

DESCRIPTION OF THE PREFERRED EMBODIMENTS

Monomer and Polymer

Any vinyl monomer is available for the chemically amplified photoresist according to the present invention in so far as the vinyl monomer is active in polymerization. From this viewpoint, it is preferable to use ethylene, a derivative of ethylene, vinyl chloride, a derivative of vinyl chloride, styrene, a derivative of styrene, acrylonitrile, a derivative of acrylonitrile, (meth)acrylate, a derivative of (meth)acrylate, norbornene carboxylic acid ester or a derivative of norbornene carboxylic acid ester for polymer. When the polymer is produced from the ethylene, a derivative of ethylene, vinyl chloride, a derivative of vinyl chloride, styrene, a derivative of styrene, acrylonitrile, a derivative of acrylonitrile, (meth)acrylate, a derivative of (meth)acrylate, norbornene carboxylic acid ester or a derivative of norbornene carboxylic acid ester, the vinyl polymer has repeated structural unit produced through the vinyl polymerization in the principal chain.

More particularly, it is preferable to use the derivatives of (meth)acrylate having the bridged alicylic δ lactone structure expressed by general formula (3) as the structural unit

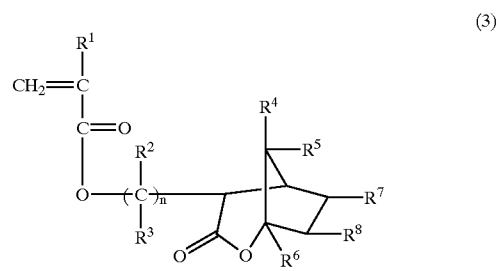

where $R^1$ is selected from the group consisting of hydrogen atom and methyl group, each of $R^2$ and $R^3$ is selected from the group consisting of hydrogen atom and alkyl groups having the carbon numbers from 1 to 4, each of $R^4$, $R^5$ and $R^6$ is selected from the group consisting of hydrogen atom and methyl group, $R^7$ and $R^8$ are hydrogen atoms or alkylene groups having the carbon number from 1 to 10 and bonded to each other for forming a ring and n is zero or 1.

When the derivative of (meth)acrylate is vinyl polymerized, the resultant polymer in the acrylic series has the bridged alicylic δ lactone structure expressed by general formula (3') in the principal chain as the repeated structural unit.

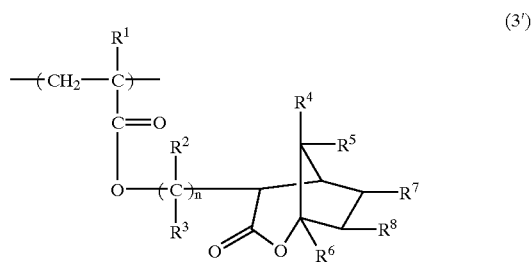

where $R^1$ is selected from the group consisting of hydrogen atom and methyl group, each of $R^2$ and $R^3$ is selected from the group consisting of hydrogen atom and alkyl groups having the carbon numbers from 1 to 4, each of $R^4$, $R^5$ and $R^6$ is selected from the group consisting of hydrogen atom and methyl group, $R^7$ and $R^8$ are hydrogen atoms or alkylene groups having the carbon number from 1 to 10 and bonded to each other for forming a ring and n is zero or 1.

The derivatives of (meth)acrylate may have alicylic lactone structure expressed by general formula (3")

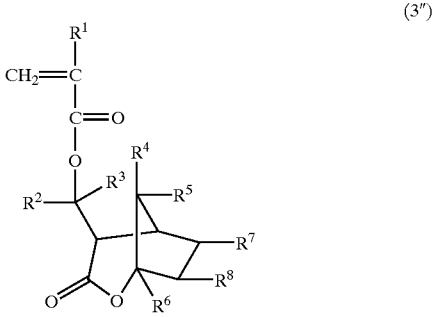

where $R^1$, $R^4$, $R^5$ and $R^6$ are hydrogen atoms or methyl groups, $R^2$ and $R^3$ are hydrogen atoms or alkyl groups having the carbon number from 1 to 4 and $R^7$ and $R^8$ are hydrogen atoms or alkylene groups bonded to each other for forming a ring. When the derivative of (meth)acrylate having the structural unit expressed by general formula (3") is polymerized, the resultant polymer has the structural unit expressed by general formula (3''') in the principal chain.

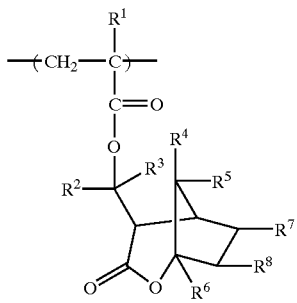
(3''')

where $R^1$, $R^4$, $R^5$ and $R^6$ are hydrogen atoms or methyl groups, $R^2$ and $R^3$ are hydrogen atoms or alkyl groups having the carbon number from 1 to 4 and $R^7$ and $R^8$ are hydrogen atoms or alkylene groups bonded to each other for forming a ring. When chemically amplified resist is produced on the basis of the polymer having the structural unit expressed by the general formula (3'''), the chemically amplified resist contains photo-acid generator. It is preferable that the polymer ranges from 70% to 99.8% by mass in the total mass of the polymer and the photo-acid generator.

Derivatives of norbornene carboxylic acid ester are also preferable. The derivatives of norbornene carboxylic acid ester have a bridged alicylic δ lactone structure expressed by general formula (4)

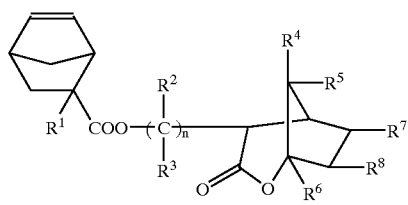
(4)

where $R^1$ is selected from the group consisting of hydrogen atom and methyl group, each of $R^2$ and $R^3$ is selected from the group consisting of hydrogen atom and alkyl groups having the carbon number from 1 to 4, each of $R^4$, $R^5$ and $R^6$ is selected from the group consisting of hydrogen atom and methyl group, $R^7$ and $R^8$ are hydrogen atoms or alkylene groups having the carbon number from 1 to 10 and bonded to each other for forming a ring and n is zero or 1.

When the derivative of norbornene carboxylic acid ester with the bridged alicylic δ lactone structure expressed by general formula (4) is polymerized, the resultant polymer has a bridged alicylic δ lactone structure expressed by general formula (4') in the principal chain as the repeated structural unit

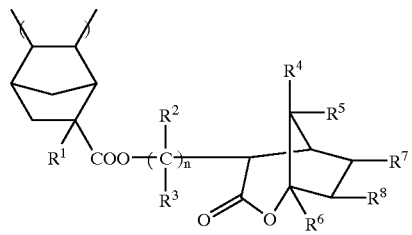
(4')

where $R^1$ is selected from the group consisting of hydrogen atom and methyl group, each of $R^2$ and $R^3$ is selected from the group consisting of hydrogen atom and alkyl groups having the carbon number from 1 to 4, each of $R^4$, $R^5$ and $R^6$ is selected from the group consisting of hydrogen atom and methyl group, $R^7$ and $R^8$ are hydrogen atoms or alkylene groups having the carbon number from 1 to 10 and bonded to each other for forming a ring and n is zero or 1.

More than one vinyl monomer may be copolymerized. When more than one vinyl monomer is copolymerized, the resultant copolymer has more than one structural unit in the principal chain as the repeated structural unit. Thus, a wide variety of desirable properties are given to the photoresist according to the present invention by using the copolymers.

As described hereinbefore, each of the $R^1$, $R^4$, $R^5$ and $R^6$ is a hydrogen atom or methyl group in the general formulae (2), (3), (4), (3') and (4'). In those general formulae, each of the $R^2$ and $R^3$ is a hydrogen atom or alkyl group having the carbon number from 1 to 4, i.e., methyl group, ethyl group, n-propyl group and n-butyl. $R^7$ and $R^8$ are hydrogen atoms or alkylene groups, which have the carbon number from 1 to 10 and are bonded to each other for forming a ring. Examples are propylene group [—(CH$_2$)$_3$—], butylene group [—(CH$_2$)$_4$—] and 1,3-cyclopentylene group.

In the general formula (1), $L^1$ is exchangeable for $R^4$, $L^2$ is exchangeable for $R^5$, $L^3$ and $L^4$ are independently exchangeable for $R^6$, $L^5$ is exchangeable for $R^7$, and $L^6$ is exchangeable for $R^8$.

For examples, in case where the derivatives of (meth) acrylate have n equal to 1, following compounds are available for the polymer and, accordingly, photoresist.

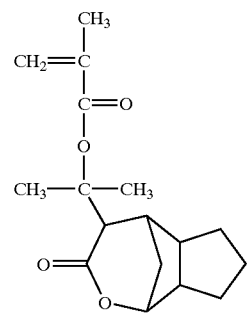

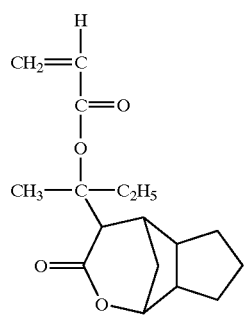
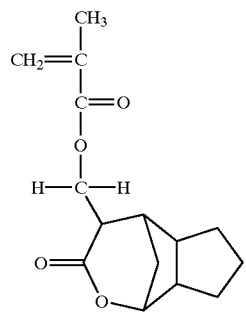
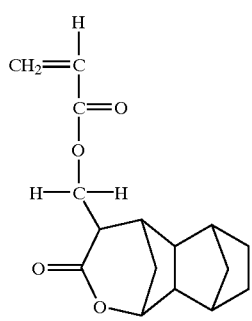
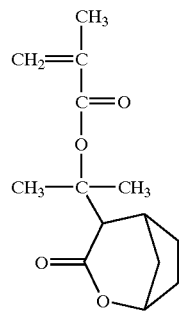
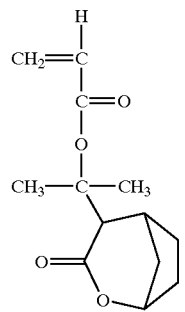
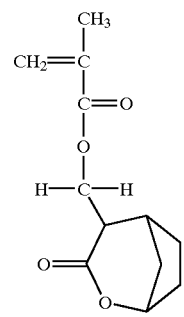
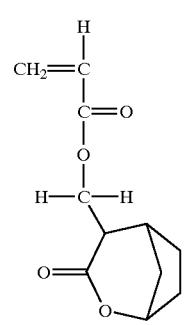
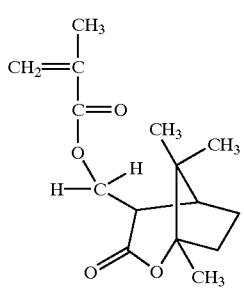
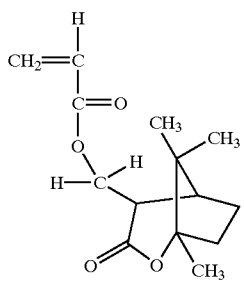

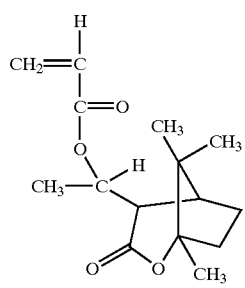
In case where the derivatives of norbornene carboxylic acid ester have n equal to 1, following compounds are available for the polymer and, accordingly, the photoresist.
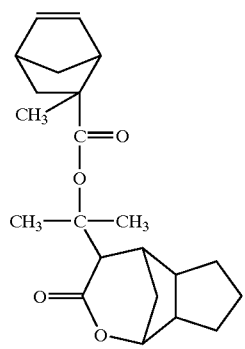
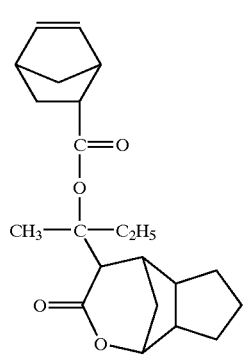
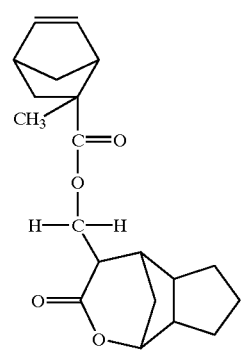
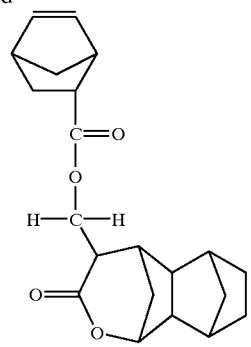
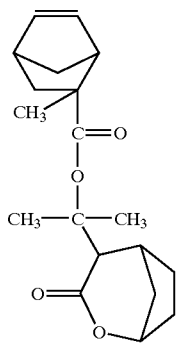
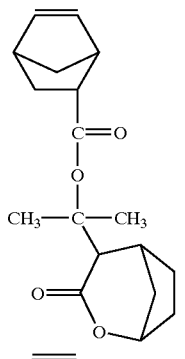
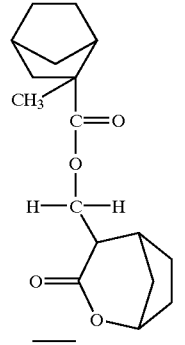
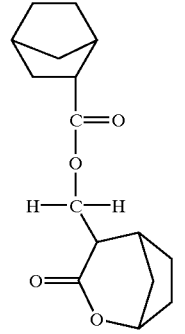

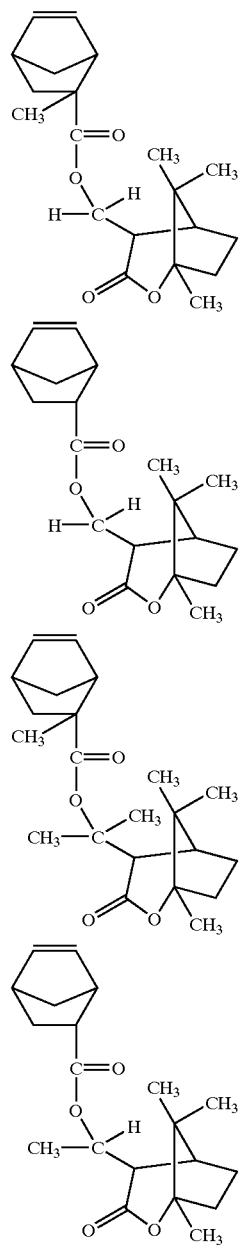
In case where the derivatives of (meth)acrylate have n equal to zero, following compounds are available for the polymer and photoresist.
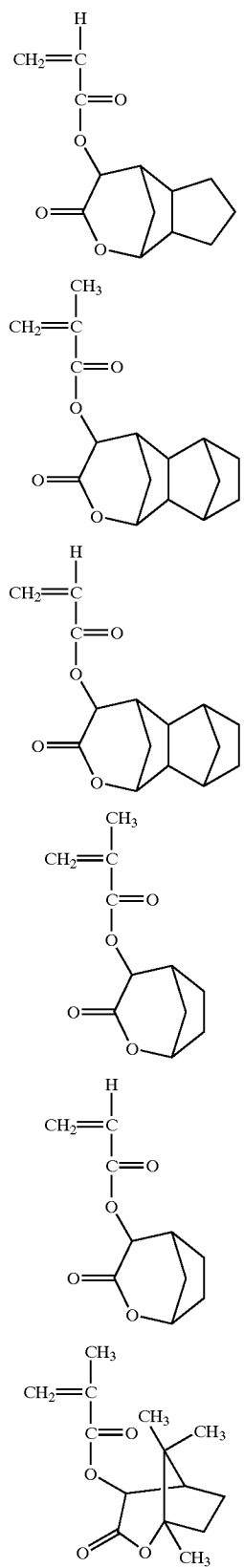

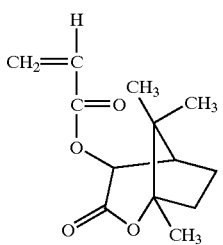

In case where the derivatives of norbornene carboxylic acid ester have n equal to zero, followings are available for the polymer and the photoresist.

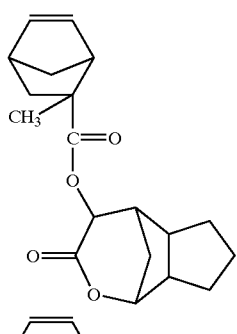

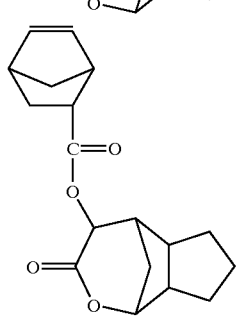

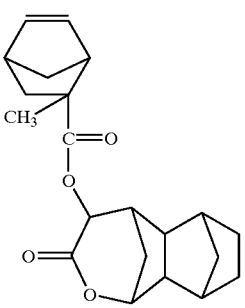

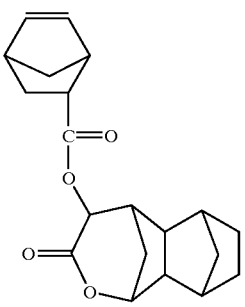

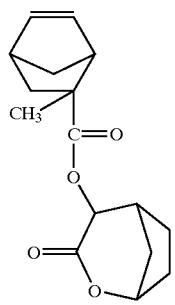

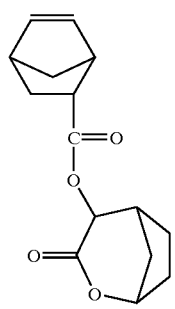

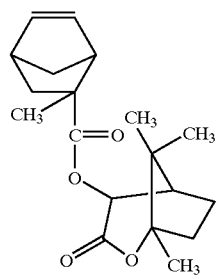

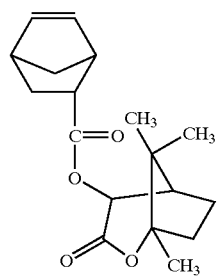

In addition to the above-described repeated structural unit, comonomer may be copolymerized so as to introduce a repeated structural unit to be decomposed by acid produced from photo-acid generator and/or another repeated structural unit expected to impart various desirable features into the polymer.

The repeated structural units, which are produced from the comonomer, are expected to exhibit a high decomposition efficiency, impart desirable features to the polymer and have good affinity to the vinyl polymerization. From these viewpoints, it is desirable to have at least one of the structural units expressed by the general formulae (3'a), (3'b) and (3'c).

(3'a)

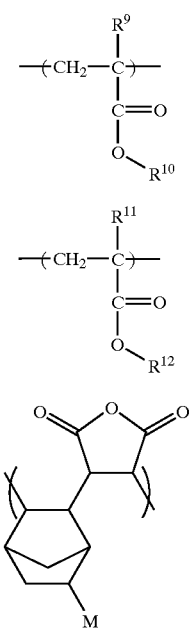

(3'b)

(3'c)

where R[9] is selected from the group consisting of hydrogen atom and methyl group, R[10] is selected from the group consisting of groups to be decomposed by acid and bridged cyclic hydrocarbon groups having the carbon number from 7 to 13 and having groups to be decomposed by acid, R[11] is selected from the group consisting of hydrogen atom and methyl group, R[12] is selected from the group consisting of hydrogen atom, hydrocarbon groups having the carbon number from 1 to 12, bridged cyclic hydrocarbon groups having the carbon number from 7 to 13 and either hydroxy or carboxy group and 2,6-norbornanecarbolactone-5-yl group and M is selected from the group consisting of hydrogen atom, hydroxy group, hydroxyalkyl groups and acid dissociated organic groups having the carbon number equal to or less than 20 and to be decomposed by acid for producing carboxy group.

R[10] is the group to be decomposed by acid or the bridged cyclic hydrocarbon groups, which have the carbon number from 7 to 13 and a group to be decomposed by acid. Examples of the group to be decomposed by acid are t-butyl, tetrahydropyran-2-yl group, tetrahydrofuran-2-yl group, 4-methoxytetrahydropyran-4-yl group, 1-ethoxyethyl group, 1-butoxyethyl group, 1-propoxyethyl group, 3-oxocyclohexyl group, 2-methyl-2-adamantyl group, 2-ethyl-2-adamantyl group, 1-methyl-1-adamantylethyl group, 8-methyl-8-tricyclo[5.2.1.0$^{2,6}$]decyl group, 1,2,7,7-tetramethyl-2-norbornyl group, 2-acetoxymentyl group, 2-hydroxymentyl group and 1-methyl-1-cyclohexylethyl group.

Examples of the bridged cyclic hydrocarbon groups having the carbon number from 7 to 13 and a group to be decomposed by acid have ester group, and are tricyclo[5.2.1.0$^{2,6}$]decyl methyl group, tricyclo[5.2.1.0$^{2,6}$]decyl group, adamantyl group, norbornyl group, methylnorbornyl group, isobornyl group, tetracyclo[4.4.0.1$^{2,5}$.1$^{7,10}$]dodecyl group and methyltetracyclo[4.4.0.1$^{2,5}$.1$^{7,10}$]dodecyl group. The chemical structures of these groups are as follows.

tricyclo[5.2.1.0$^{2,6}$]decyl methyl group

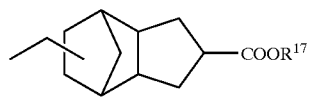

or with ester group,

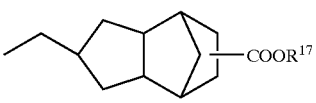

tricyclo[5.2.1.0$^{2,6}$]decyl group

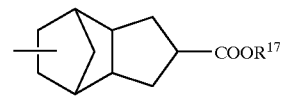

or with ester group,

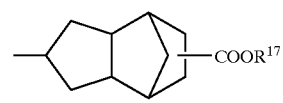

adamantyl group,

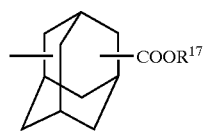

with ester group,
norbornyl group

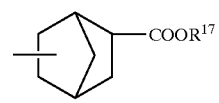

with ester group,
methylnorbornyl group

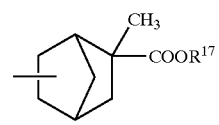

with ester group,
isobornyl group

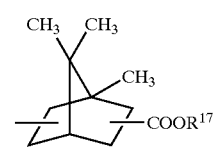

with ester group, tetracyclo[4.4.0.1$^{2,5}$.1$^{7,10}$]dodecyl group

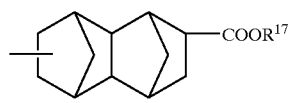

with ester group,
methyltetracyclo[4.4.0.1$^{2,5}$.1$^{7,10}$]dodecyl group

with ester group,

In the chemical structures, R$^{17}$ is the group to be decomposed by acid, and examples of the group are t-butyl, tetrahydropyran-2-yl group, tetrahydrofuran-2-yl group, 4-methoxytetrahydropyran-4-yl group, 1-ethoxyethyl group, 1-butoxyethyl group, 1-propoxyethyl group, 3-oxocyclohexyl group, 2-methyl-2-adamantyl group, 2-ethyl-2-admantyl group, 8-methyl-8-tricyclo[5.2.1.0$^{2,6}$] decyl group, 1,2,7,7-tetramethyl-2-norbornyl group, 2-acetoxymenthyl group, 2-hydroxymenthyl group and 1-methyl-1-cyclohexylethyl group.

In case where R$^{12}$ is a hydrocarbon group having the carbon number from 1 to 12, examples of R$^{12}$ are methyl group, ethyl group, n-propyl group, isopropyl group, n-butyl group, isobutyl group, t-butyl group, cyclohexyl group, tricyclo[5.2.1.0$^{2,6}$]decyl group, adamantyl group, norbornyl group, isobornyl group and tetracyclo[4.4.0.1$^{2,5}$.1$^{7,10}$] dodecyl group.

Examples of the bridged cyclic hydrocarbon having the carbon number from 7 to 13 and one of the hydroxy group and carboxy group are hydroxyadamantyl group, dihydroxyadamantyl group, hydroxynorbornyl group, hydroxytetracyclododecyl group, carboxyadamantyl group, carboxynorbornyl group and carboxytetracyclododecyl group.

In case where M is hydroxyalkyl group, examples of M are hydroxymethyl group and hydroxyethyl group.

In case where M is the acid dissociated organic group having the carbon number equal to or less than 20 and to be decomposed by acid for producing carboxy group, examples of M are t-butoxycarbonyl group, tetrahydropyranyloxycarbonyl group, tetrahydrofuranyloxycarbonyl group, 4-methoxy tetorahydropyranyloxycarbonyl group, 1-ethoxyethoxycarbonyl group, 1-butoxyethoxycarbonyl group, 1-propoxyethoxycarbonyl group, 3-oxocyclohexyloxycarbonyl group, 2-methyl-2-admantyloxycarbonyl group, 2-ethyl-2-adamantyloxycarbonyl group, 8-methyl-8-tricyclo[5.2.1.0$^{2,6}$]decyloxycarbonyl group, 1,2,7,7-tetramethyl-2-norbornyloxycarbonyl group, 2-acetoxymenthyloxycarbonyl group, 2-hydroxymenthyloxycarbonyl group and 1-methyl-1-cyclohexylethoxycarbonyl group.

Other repeated structural units are expected to enhance the decomposition efficiency and/or give the photoresist other desirable features. Comonomers for these repeated structural units are to be well polymerized for producing vinyl polymer. From this viewpoint, at least one of the structural units expressed by the general formulae (4'a), (4'b) and (4'c) is preferable.

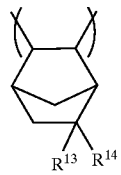

(4'a)

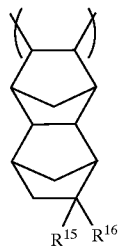

(4'b)

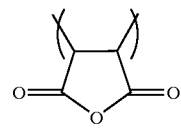

(4'c)

where R$^{13}$ is selected from the group consisting of hydrogen atom and methyl group, R$^{14}$ is selected from the group consisting of hydroxy group, hydroxyalkyl group and acid dissociated organic groups having the carbon number equal to or less than 20 and to be decomposed by acid for producing carboxy group, R$^{16}$ is selected from the group consisting of hydrogen atom and methyl group and R$^{16}$ is selected from the group consisting of hydroxy group, hydroxyalkyl group and acid dissociated organic groups having the carbon number equal to or less than 20 and to be decomposed by acid for producing carboxy group.

Each of R$^{14}$ and R$^{16}$ is hydroxy group, hydroxyalkyl group such as hydroxymethyl group and hydroxyethyl group or acid dissociated organic groups having the carbon number equal to or less than 20 and to be decomposed by acid for producing carboxy group. The group of acid dissociated organic groups contains t-butoxycarbonyl group, tetrahydropyranyloxycarbonyl group, tetrahydrofuranyloxycarbonyl group, 4-methoxytetrahydropyranyloxycarbonyl group, 1-ethoxyethoxycarbonyl group, 1-butoxyethoxycarbonyl group, 1-propoxyethoxycarbonyl group, 3-oxocyclohyxyloxycarbonyl group, 2-methyl-2-adamantyloxycarbonyl group, 2-ethyl-2-adamantyloxycarbonyl group, 8-methyl-8-tricyclo[5.2.1.0$^{2,6}$]decyloxycarbonyl group, 1,2,7,7-tetramethyl-2-norbornyloxycarbonyl group, 2-acetoxymenthyloxycarbonyl group, 2-hydroxymenthyloxycarbonyl group and 1-methyl-1-cyclohexylethoxycarbonyl group.

From the viewpoint of desirable properties of resultant copolymer, it is preferable to copolymerize each of the repeated structural units expressed by the general formulae (3'a), (3'b) and (3'c) with at least one of the repeated structural unit expressed by the general formulae (4'a), (4'b) and (4'c). It is also preferable to copolymerize each of the repeated structural units expressed by the general formulae (4'a), (4'b) and (4'c) with at least one of the repeated structural unit expressed by the general formulae (3'a), (3'b) and (3'c). The repeated structural units expressed by the general formulae (3'a) to (3'c) may be selectively incorporated in the polymer concurrently with the repeated structural units expressed by the general formulae (4'a) to (4'c) so as to give a wide variety of desirable properties to the polymer.

It is preferable that the copolymer contains at least one of the repeated structural units expressed by the general formulae (3') and (4') fallen within the range between 5 mole % and 90 mole % from the viewpoint of the properties of the resultant polymer. It is more preferable that at least one of the repeated structural units expressed by the general formulae (3') and (4') is fallen within the range between 7 mole % and 80 mole %. It is much more preferable that at least one of the repeated structural units expressed by the general formulae (3') and (4') is fallen within the range between 10 mole % and 70 mole %.

Since the repeated structural units expressed by the general formulae (3'a) to (3'c) well react with the derivatives of (meth)acrylate expressed by the general formula (3), it is preferable to make the repeated structural unit or units expressed by the general formulae (3'a) to (3'c) copolymerized with the repeated structural unit expressed by the general formula (3'). In this instance, it is preferable that the structural unit expressed by general formula (3') is fallen within the range between 5 mole % and 90 mole % of the copolymer. It is more preferable that the structural unit expressed by general formula (3') is fallen within the range between 7 mole % and 80 mole % of the copolymer. It is much more preferable that the structural unit expressed by general formula (3') is fallen within the range between 10 mole % and 70 mole % of the copolymer.

Since the repeated structural units expressed by the general formulae (4'a) to (4'c) well react with the derivatives of norbornene carboxylic acid ester expressed by the general formula (4), it is preferable to make the repeated structural unit or units expressed by the general formulae (4'a) to (4'c) copolymerized with the repeated structural unit expressed by the general formula (4'). In this instance, it is preferable that the structural unit expressed by general formula (4') is fallen within the range between 5 mole % and 90 mole % of the copolymer. It is more preferable that the structural unit expressed by general formula (4') is fallen within the range between 7 mole % and 80 mole % of the copolymer. It is much more preferable that the structural unit expressed by general formula (4') is fallen within the range between 10 mole % and 70 mole % of the copolymer.

The polymers described hereinbefore are produced through a usual polymerization process such as, for example, the radical polymerization, anionic polymerization or addition polymerization. A suitable polymerization initiator such as, for example, azobisisobutyronitrile (AIBN) is, by way of example, added to dry tetrahydrofuran in inert atmosphere such as argon or nitrogen, and the polymerization initiator and the dry tetrahydrofuran are agitated at 50 degrees to 70 degrees in centigrade for 0.5 hour to 12 hours. Then, the polymer is produced through the radical polymerization.

In case where the polymer is produced through the addition polymerization, the polymer may be produced through the process disclosed by J. P. Mathew, Macromolecules, vol. 29, pages 2755 to 2763, 1996. Namely, suitable catalyst in palladium compound series is used in the addition polymerization. $(\eta^3$-allyl) Pd(BF$_4$), $(\eta^3$-allyl) Pd (SbF$_6$) and [Pd (CH$_3$CN)$_4$] (BF$_4$)$_2$ are examples of the palladium compound catalyst. Otherwise, nickel compound catalyst such as bis (pentafluorophenyl) nickel toluene complex is used in the addition polymerization as taught by T. Chiba et. al, Journal of Photopolymer Science and Technology, vol. 13, No. 4, pages 657 to 664, 2000.

The weight average molecular weight of the polymer available for the photoresist according to the present invention is fallen within the range from 2,000 to 200,000.

Chemically Amplified Resist

Chemically amplified resist embodying the present invention contains at least the polymer described hereinbefore and photo-acid generator. In case where n and both of $R^2$ and $R^3$ are 1 and alkyl group in the structural unit expressed by the general formula (3'), the alicyclic lactone unit is a tertiary ester of carboxylic acid, and is eliminated in the presence of acid. Thus, it is an acid decomposed group. The reaction is as follows.

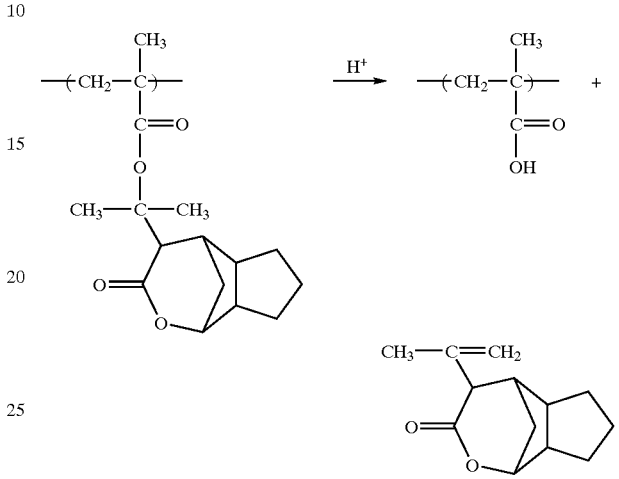

It is preferable that the photo-acid generator generates acid in the presence of the light equal in wavelength to or less than 400 nanometers. It is more preferable to produce the acid in the presence of the light having the wavelength between 180 nanometers and 220 nanometers. There is not any limit to the photo-acid generator in so far as liquid mixture, in which the mixture containing the photo-acid generator and the polymer such as the polymer in acrylic series is well dissolved in organic solvent, is uniformly spread by using a spin coater, by way of example. More than one photo-acid generator may be mixed with the polymer.

Examples of the photo-acid generator are derivatives of triphenylsulfonium salt, derivatives of diphenyliodonium salt, derivatives of dialkylphenacylsulfonium salt, derivatives of nitrobenzylsulfonate and derivatives of sulfonic acid ester of N-hydroxysuccinimide.

Another photo-acid generator is disclosed by J. V. Crivello et. al, Journal of the Organic Chemistry, vol. 43, No. 15, pages 3055 to 3058, 1978. J. V. Crivello et. al. teach derivatives of triphenylsulfonium salt and other onium salts such as sulfonium salt, iodonium salt, phosphonium salt, diazonium salt and ammonium salt. Yet another photo-acid generator is disclosed by O. Nalamasu et. al, SPIE Proceedings, vol. 1262, page 32, 1990. O. Nalamasu et. al. teach 2,6-dinitrobenzyl esters. Still another photo-acid generator is disclosed by Takumi Ueno et. al, Proceedings of PME'89, Kohdansha, pages 413 to 424, 1990, and Ueno et. al. teach 1,2,3-tri(methanesulfonyloxy)benzen. Yet another photo-acid generator is disclosed in Japanese Patent Application laid-open No. 5-134416, and is sulfosuccinimide.

From the viewpoint that the photo-acid generator makes the chemically amplified resist well sensitive to the exposure light for producing a fine latent image therein, it is preferable that the content of the photo-acid generator is equal to or greater than 0.2% by mass of both polymer and photo-acid generator. It is more preferable that the chemically amplified resist contains the photo-acid generator equal to or greater than 1% by mass of both polymer and photo-acid generator.

However, if the content of photo-acid generator is greater than 30% by mass, the chemically amplified resist is less liable to be uniformly spread, and the scum is not ignorable after the development. Thus, the upper limit of the content is 30% by mass. It is more preferable that the content of the photo-acid generator is equal to or less than 15% by mass. Thus, the photo-acid generator is to range from 0.2% by mass to 30% by mass, and the more preferable range is between 1% by mass and 15% by mass.

When the manufacturer prepares the chemically amplified resist, appropriate solvent is used. Any organic solvent is available for the chemically amplified resist in so far as the polymer and the photo-acid generator are well dissolved therein for being uniformly spread over substrates. Only one sort of solvent or more than one sort of solvent is used for preparing the chemically amplified resist according to the present invention.

Examples of the solvent are n-propyl alcohol, iso-propyl alcohol, n-butyl alcohol, tert-butyl alcohol, propylene glycol monomethylether acetate, propylene glycol monoethylether acetate, methyl cellosolve acetate, ethyl cellosolve acetate, ethyl lactate, methyl lactate, 2-methoxybutyl acetate, 2-ethoxyethyl acetate, methyl, pyruvate, ethyl pyruvate, 3-methoxy methyl propionate, 3-methoxy ethyl propionate, N-methyl-2-pyrrolidinone, cyclohexanone, cyclopentanone, cyclohexanol, methyl ethyl ketone, 1,4-dioxane, ethyleneglycolmonomethylether, ethyleneglycolmonomethylether acetate, ethyleneglycolmonoethylether, ethyleneglycolmonoisopropylether, diethyleneglycolmonomethylether and diethyleneglicoldimethylether.

The chemically amplified resist according to the present invention may further contain other additives such as, for example, dissolution inhibitor, organic base, surface active agent, dyestuff, stabilizer, coating property improving agent and coloring agent.

Pattern Transfer

A pattern image is transferred from a photo-mask to a chemically amplified resist layer as follows. First, the chemically amplified resist described hereinbefore is prepared. The chemically amplified resist solution is spread over a layer such as, for example, a semiconductor wafer or a semiconductor/insulating layer on the semiconductor wafer. A spin coater may be used for spreading the chemically amplified resist solution.

Subsequently, the chemically amplified resist layer is pre-baked, and, thereafter, the semiconductor wafer is inserted into a chamber of an aligner. The aligner is well known to skilled person, and no further description is hereinbelow incorporated. Laser light is radiated from a light source to a photo-mask. The laser light has the wavelength between 180 nanometers and 220 nanometers. In this instance, the light source radiates 193 nanometer wavelength ArF excimer laser light. The ArF excimer laser light passes through the photo-mask, and carries the pattern image on the photo-mask. The image-carrying light reaches the chemically amplified resist layer. The image-carrying light produces a latent image in the chemically amplified resist layer.

The semiconductor wafer is taken out from the aligner, and the latent image is developed. Then, the chemically amplified resist layer is patterned into a resist mask. Using the resist mask, the semiconductor/insulating layer is, by way of example, selectively etched. Otherwise, dopant impurity may be ion implanted into the semiconductor/insulting layer or semiconductor wafer. Thus, the semiconductor device manufactures form miniature patterns on or over the semiconductor wafers.

Description is hereinbelow made on several examples. However, these examples do not set any limit to the scope of the present invention. Highpurity reagents and other chemicals used in the examples were purchased in the market. However, when special reagent or chemical was used, the special reagent/chemical is detailed.

FIRST EXAMPLE

The present inventors synthesized methacrylate, i.e., Methacrylate 1 through the following reaction formula.

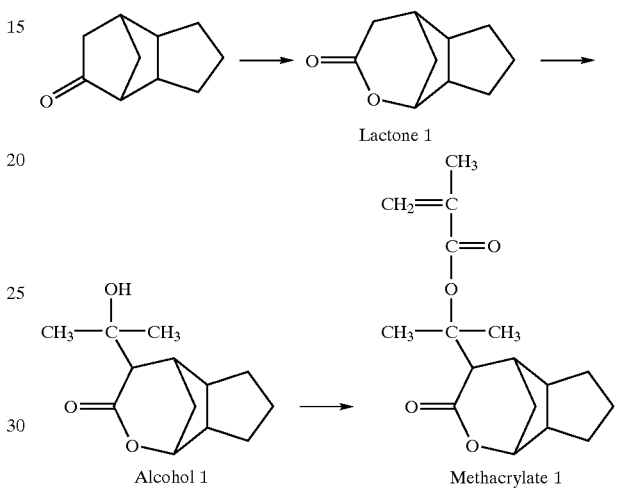

The methacrylate, i.e., Methacrylate 1 was expressed by the general formula (3) where $R^1$, $R^2$ and $R^3$ were methyl groups, $R^4$, $R^5$ and $R^6$ were hydrogen atoms, $R^7$ and $R^8$ were propylene groups, i.e., $[-(CH_2)_3-]$ bonded to each other for forming a ring and n was 1.

In detail, 25.4 grams of tricyclodecane-8-one was dissolved in 150 milliliters of methylene chloride, and 42.6 grams of sodium hydrogen carbonate was added to the resultant solution. 50 grams of m-chloroperbenzoic acid dissolved in 400 milliliters of methylene chloride was further dropped into the resultant solution. The resultant solution was agitated all night at room temperature. Then, sodium m-chlorobenzoate acid was deposited, and was filtrated. The filtrate was washed in 5% water solution of sodium sulfite, thereafter, in 5% water solution of sodium carbonate and, finally, in brine. The organic layer was dried with $MgSO_4$, and methylene chloride was eliminated in vacuum therefrom. The residue was distilled in vacuum, i.e., 0.35 mm Hg at 1 10 degrees to 111 degrees in centigrade. Then, 24.8 grams of lactone 1 was obtained. The yield was 88%.

Subsequently, 140 milliliters of dry THF was cooled to −78 degrees in centigrade, and 70 milliliters of 2 mole/1 THF solution of lithium diisopropyl amide was dropped thereinto in argon atmosphere. 10 grams of the lactone compound, i.e., Lactone 1, was dissolved in 20 milliliters of dry THF, and the resultant solution was further dropped thereinto. Reaction proceeded for an hour at −78 degrees in centigrade, and 26.6 grams of acetone was dropped thereinto. The resultant solution was agitated for 4 hours, and 10% hydrochloric acid water solution was added to the resultant solution until the solution was changed to acid. An organic layer was extracted from the solution by using 300 milliliters of ethyl acetate. The organic layer was washed in 5% of sodium hydrogen carbonate and, thereafter, in brine. After the washing, the organic layer was dried with magnesium sulfate, and the solvent was eliminated in vacuum. Hexane was added to the residue, and, thereafter, cooled. Then, a piece of crystal was precipitated, and was filtered. 6.04 grams of alcohol compound, i.e., Alcohol 1 was obtained. The yield was 24%.

7 grams of alcohol, 3.79 grams of triethylamine and 9 milligram of phenothiazine were dissolved in 30 milliliters of dry methylene chloride, and solution, in which 3.26 grams of methacryloyl chloride was dissolved in 5 milliliters of dry methylane chloride, was dropped into the resultant solution cooled with ice. The resultant solution was continuously cooled with ice for 3 hours, and, thereafter, was agitated through all night at room temperature.

Subsequently, 200 milliliters of ethyl acetate was added, and an organic layer was obtained. The organic layer was washed in 0.5 N hydrochloric acid, thereafter, in 3% water solution of sodium hydrogen carbonate and, finally, in brine. The organic layer was dried with magnesium sulfate, and the solvent was eliminated in vacuum. The residue was separated and refined through a silica gel column. Elute contained hexane and ethyl acetate at 5:1.2.4 grams of methacrylate, i.e., Methacrylate 1 was obtained. The yield was 26%.

The methacrylate was analyzed. The result of $^1$H-NMR (CDCl$_3$) was as follows; δ was 0.84 to 1.0 (1H, m), 1.0 to 1.13 (1H, m), 1.66 (3H, s), 1.78 (3H, s), 1.91 (3H, s), 1.27 to 1.41 (1H, m), 1.67 to 1.75 (2H, m), 1.94 to 2.13 (3H, m), 2.25 to 2.41 (2H, m), 2.75 (1H, q), 3.06 (1H, s), 4.49 (1H, s), 5.54 (1H, s) and 6.04 (1H, s).

The result of 1R (KBr) was as follows; 2850, 2950 (υC—H), 1712, 1728 (υC=O), 1632 (υC=C) and 1136, 1184 (υC-O)cm$^{-1}$.

SECOND EXAMPLE

The present inventors synthesized acrylate expressed as follows.

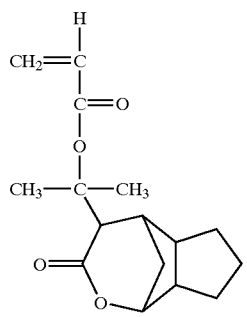

The acrylate was expressed by the general formula (3) where where $R^1$, $R^4$, $R^5$ and $R^6$ were hydrogen atoms, $R^2$ and $R^3$ were methyl groups, $R^7$ and $R^8$ were propylene groups, i.e., [—(CH$_2$)$_3$—] bonded to each other for forming a ring and n was 1.

The acrylate was synthesized as similar to the synthesis of the methacrylate except that the methacryloyl chloride was replaced with acryloyl chloride. The yield was 21%.

The acrylate was analyzed. The result of $^1$H-NMR (CDCl$_3$) was as follows; δ was 0.87 to 1.12 (2H, m), 1.24 to 1.42 (1H, m), 1.62 (3H, s), 1.78 (3H, s), 1.65 to 1.77 (2H, m), 1.90 to 2.11 (2H, m), 2.26 to 2.41 (3H, m), 2.75 (1H, q), 3.17 (1H, s), 4.48 (1H, s), 5.58 (1H, d), 6.03 (1H, dd) and 6.34 (1H, d).

The result of 1R (KBr) was as follows; 2850, 2950 (υC—H), 1720 (υC=O), 1616, 1632 (υC=C) and 1140, 1192 (υC—O) cm$^{-1}$.

THIRD EXAMPLE

The present inventors further synthesized acrylate, i.e., Acrylate 1 through the following reaction formula.

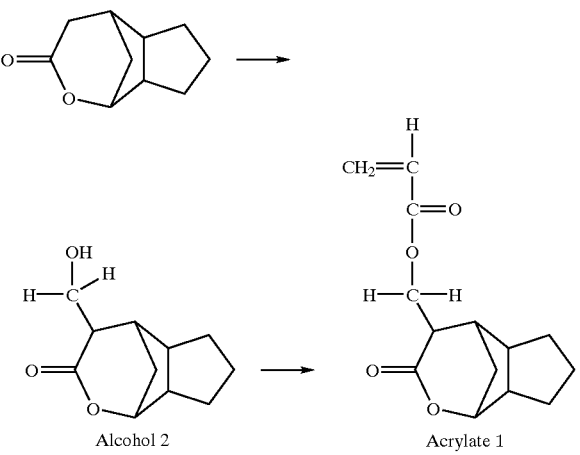

Alcohol 2        Acrylate 1

The acrylate, i.e., Acrylate 1 was expressed by the general formula (3) where $R^1$, $R^2$, $R^3$, $R^4$, $R^5$ and $R^6$ were hydrogen atoms, $R^7$ and $R^8$ were propylene groups, i.e., [—(CH$_2$)$_3$—] bonded to each other for forming a ring and n was 1.

The synthesis for the acrylate was similar to that for the first example except that the acetone was replaced with formaldehyde in the synthesis of the alcohol compound, i.e., Alcohol 2 and that the methacryloyl chloride was replaced with acryloyl chloride. The yield was 18%

The acrylate was analyzed. The result of $^1$H-NMR (CDCl$_3$) was as follows; δ was 0.88 to 1.19 (2H, m), 1.28 to 1.43 (1H, m), 1.56 to 1.85 (2H, m), 1.93 to 2.11 (3H, m), 2.16 to 2.22 (1H, m), 2.34 to 2.45 (1H, m), 2.69 to 2.87 (2H, m), 4.44 (1H, d), 4.46 (1H, d), 4.51 (1H, s), 5.88 (1H, d), 6.14 (1H, dd) and 6.44 (1H, d).

The result of IR (KBr) was as follows; 2866, 2954 (υC—H), 1732 (υC=O), 1635 (υC=C) and 1189 (υC—O) cm$^{-1}$.

FOURTH EXAMPLE

The present inventors synthesized polymer, which contained a structural unit expressed by the general formula (3') at 50 mole % and another structural unit expressed by the general formula (3'b) at 50 mole %. These structural units were as follows.

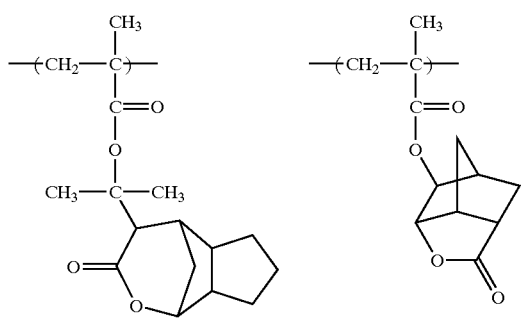

The first structural unit was expressed by the general formula (3') where $R^1$, $R^2$ and $R^3$ were methyl groups, $R^4$, $R^5$ and $R^6$ were hydrogen atoms, $R^7$ and $R^8$ were propylene groups, i.e., [—$(CH_2)_3$—] bonded to each other for forming a ring and n was 1. The second structural unit was expressed by the general formula (3'b) where $R^{11}$ was methyl group and $R^{12}$ was 2,6-norbornanecarbolactone-5-yl group.

The synthesis proceeded as follows. 2.4 grams of methacrylate, which was obtained through the synthesis for the first example, and 1.82 grams of 5-methacryloyloxy-2, 6-norbornanecarbolactone were dissolved in 22 milliliters of dry tetrahydrofuran in a 100 ml flask. 108 milligrams of AIBN was added thereto, and was agitated in argon atmosphere at 60 degrees to 65 degrees in centigrade. After 3 hours, the solution was cooled, and the reactant mixture was poured into 400 milliliters of methanol. Deposited precipitate was filtrated. The filtrate was refined, gain. Thus, 2.95 grams of the polymer was obtained. The yield was 70%.

The polymer was analyzed. The copolymerization ratio was 50:50 on the basis of the integral ratio of $^1$H-NMR. From the result of GPC analysis, weight average molecular weight (Mw) was 9600 (polystyrene), and the degree of dispersion (Mw/Mn) was 1.83.

FIFTH EXAMPLE AND SIXTH EXAMPLE

The fifth and sixth examples were polymerized as similar to the fourth example except for the ratio of the monomers as shown in the following table.

|  | Ratio of Monomers | Copolymerization Ratio (by mole) | Weight Average Molecular Weight |
|---|---|---|---|
| Fifth Example | 0.3/0.7 | 0.31/0.69 | 8500 |
| Sixth Example | 0.7/0.3 | 0.7/0.3 | 10800 |

SEVENTH EXAMPLE AND EIGHTH EXAMPLE

The seventh and eighth examples were polymerized as similar to the fourth example except for the amount of AIBN, i.e., concentration. AIBN concentration, copolymerization ratio and weight average molecular weight were as follows.

|  | AIBN Concentration | Copolymerization Ratio (by mole) | Weight Average Molecular Weight |
|---|---|---|---|
| Seventh Example | 0.5 mole % | 0.5/0.5 | 45000 |
| Eighth Example | 10 mole % | 0.49/0.51 | 4100 |

NINTH EXAMPLE

The present inventors synthesized polymer in acrylic series. The polymer contained a structural unit expressed by the general formula (3') at 50 mole % and another structural unit expressed by the general formula (3'a) at 50 mole %. These structural units were as follows.

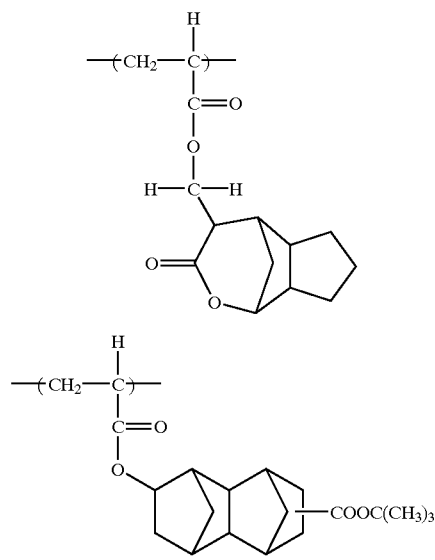

The first structural unit was expressed by the general formula (3') where $R^1$, $R^2$, $R^3$, $R^4$, $R^5$ and $R^6$ were hydrogen atoms, $R^7$ and $R^8$ were propylene groups, i.e., [—$(CH_2)_3$—] bonded to each other for forming a ring and n was 1. The second structural unit was expressed by the general formula (3'a) where $R^9$ was hydrogen atom and $R^{10}$ was t-butoxycarbonyltetracyclododecyl group.

The synthesis was similar to that for the fourth example except that the present inventors used the monomer of the third example and t-buthoxycarbonyl-tetracyclododecyl acrylate instead of the monomer of the first example and 5-methacryloyloxy-2,6-norbornanecarbolactone. The yield was 54%, and the weight average molecular weight Mw was 10800. The degree of dispersion Mw/Mn was 1.84.

TENTH EXAMPLE

The present inventors synthesized polymer in acrylic series. The polymer contained a structural unit expressed by the general formula (3') at 50 mole % and another structural unit expressed by the general formula (3'a) at 50 mole %. These structural units were as follows.

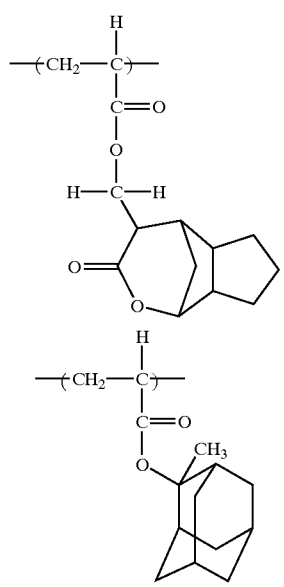

The first structural unit was expressed by the general formula (3') where $R^1$, $R^2$, $R^3$, $R^4$, $R^5$ and $R^6$ were hydrogen atoms, $R^7$ and $R^8$ were propylene groups, i.e., [—$(CH_2)_3$—] bonded to each other for forming a ring and n was 1. The second structural unit was expressed by the general formula (3'a) where $R^9$ was hydrogen atom and $R^{10}$ was 2-methyl-2-adamantyl group.

The synthesis was similar to that for the ninth example except that the present inventors used 2-methyl-2-adamantyl acrylate instead of t-butoxycarbonyltetracyclododecyl acrylate. The yield was 51%, and the weight average molecular weight Mw was 9100. The degree of dispersion Mw/Mn was 1.92.

ELEVENTH EXAMPLE

The present inventors synthesized polymer in acrylic series. The polymer contained a structural unit expressed by the general formula (3') at 30 mole %, another structural unit expressed by the general formula (3'a) at 50 mole % and yet another structural unit expressed by the general formula (3'b) at 20 mole %. These structural units were as follows.

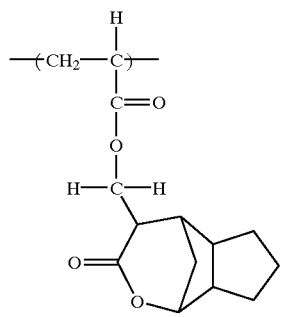

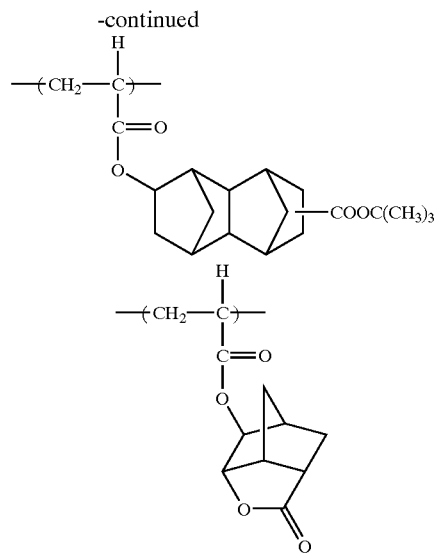

The first structural unit was expressed by the general formula (3') where $R^1$, $R^2$, $R^3$, $R^4$, $R^5$ and $R^6$ were hydrogen atoms, $R^1$ and $R^8$ were propylene groups, i.e., [—$(CH_2)_3$—] bonded to each other for forming a ring and n was 1. The second structural unit was expressed by the general formula (3'a) where $R^9$ was hydrogen atom and $R^{10}$ was t-butoxycarbonyltetracyclododecyl group. The third structural unit was expressed by the general formula (3'b) where $R^{11}$ was hydrogen atom and $R^{12}$ was 2,6-norbornanecarbolactone-5-yl group.

The synthesis was similar to that for the fourth example. In the synthesis, the monomer of the third example, t-butoxycarbonyltetracyclododecyl acrylate and 5-acryloyloxy-2,6-norbornanecarbolactone were used. The yield was 57%, and the weight average molecular weight Mw was 8700. The degree of dispersion Mw/Mn was 1.76.

TWELFTH EXAMPLE

The present inventors synthesized polymer in acrylic series. The polymer contained a structural unit expressed by the general formula (3') at 30 mole %, another structural unit expressed by the general formula (3'a) at 50 mole % and yet another structural unit expressed by the general formula (3'b) at 20 mole %. These structural units were as follows.

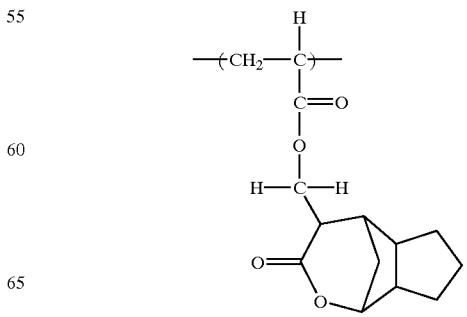

-continued

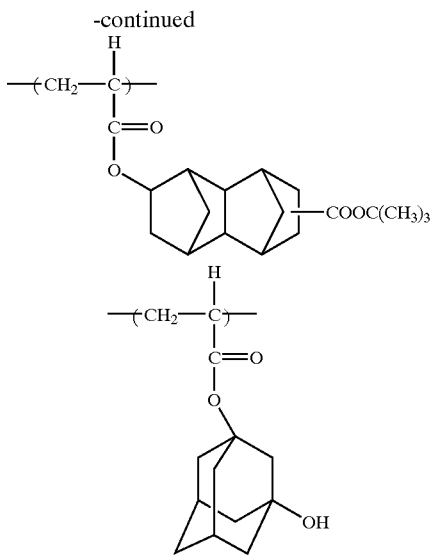

The first structural unit was expressed by the general formula (3') where $R^1$, $R^2$, $R^3$, $R^4$, $R^5$ and $R^6$ were hydrogen atoms, $R^7$ and $R^8$ were propylene groups, i.e., [—$(CH_2)_3$—] bonded to each other for forming a ring and n was 1. The second structural unit was expressed by the general formula (3'a) where $R^9$ was hydrogen atom and $R^{10}$ was t-butoxycarbonyltetracyclododecyl group. The third structural unit was expressed by the general formula (3'b) where $R^{11}$ was methyl group and $R^{12}$ was 3-hydroxy-1-admantyl group.

The synthesis was similar to that for the fourth example. In the synthesis, the monomer of the third example, t-butoxycarbonyltetracyclododecyl acrylate and 3-hydroxy-1-adamantylmethacrylate were used. The yield was 48%, and the weight average molecular weight Mw was 10500. The degree of dispersion Mw/Mn was 2.02.

THIRTEENTH EXAMPLE

The present inventors synthesized polymer in acrylic series. The polymer contained a structural unit expressed by the general formula (3') at 50 mole % and another structural unit expressed by the general formula (3'c) at 50 mole %. These structural units were as follows.

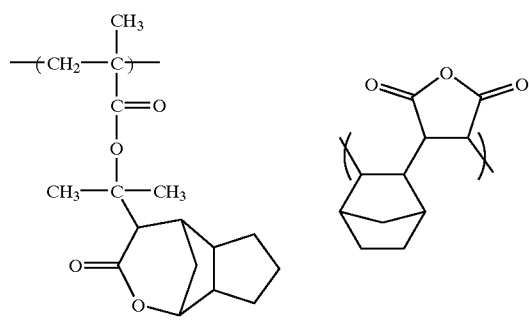

The first structural unit was expressed by the general formula (3') where $R^1$, $R^2$ and $R^3$ were methyl groups, $R^4$, $R^5$ and $R^6$ were hydrogen atoms, $R^7$ and $R^8$ were propylene groups, i.e., [—$(CH_2)_3$—] bonded to each other for forming a ring and n was 1. The second structural unit was expressed by the general formula (3'c) where M was hydrogen atom.

The synthesis was similar to that for the fourth example. In the synthesis, the monomer of the first example, nor- bornene and maleic anhidride were used. The yield was 26%, and the weight average molecular weight Mw was 5600. The degree of dispersion Mw/Mn was 2.24.

FOURTEENTH EXAMPLE

The present inventor synthesized a derivative of norbornene expressed as follows.

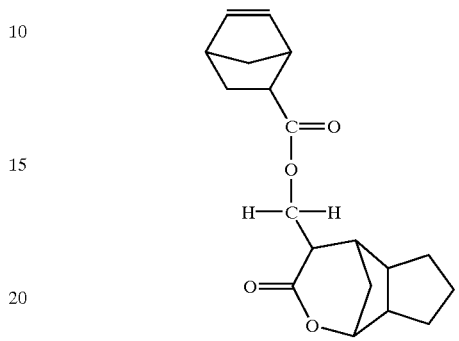

The derivative of norbornene was expressed by the general formula (4) where $R^1$, $R^2$, $R^3$, $R^4$, $R^5$ and $R^6$ were hydrogen atoms, $R^7$ and $R^8$ were propylene groups, i.e., [—$(CH_2)_3$—] bonded to each other for forming a ring and n was 1.

The derivative was synthesized as follows. 20 grams of the derivative of acrylate obtained as the third example was dissolved in 20 milliliters of toluene. 7 grams of cyclopentadiene was dropped into the solution cooled with ice, and was agitated through all night. Dicyclopentadiene was produced as byproduct, and was eliminated in vacuum. Then, 24.9 grams of the derivative of norbornene was obtained. The derivative of norbornene was viscous liquid, and the yield was 95%.

The derivative of norbornene was analyzed. The result of $^1$H-NMR ($CDCl_3$) was as follows; δ was 0.84 to 1.17 (2H, m), 1.19 to 1.53 (4H, m), 1.65 to 2.45 (8H, m), 2.64 to 3.3 (4H, m), 4.16 to 4.4 (2H, m), 4.5 (1H, s), 5.8 to 5.98 (1H, m) and 6.1 to 6.3 (1H, m). The result of 1R(KBr) was as follows; 2951, 2866 (υC—H), 1843, 1721 (υC=O), 1185 (υC—O) $cm^{-1}$.

FIFTEENTH EXAMPLE

The present inventors further synthesized another derivative of norbornene expressed as follows.

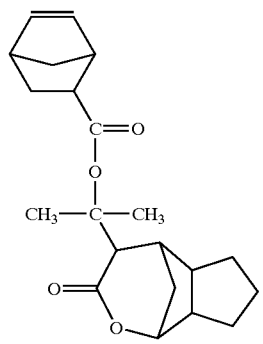

The derivative of norbornene was expressed by the general formula (4) where $R^1$, $R^4$, $R^5$ and $R^6$ were hydrogen atoms, $R^2$ and $R^3$ were methyl groups, $R^7$ and $R^8$ were propylene groups, i.e., [—(CH$_2$)$_3$—] bonded to each other for forming a ring and n was 1.

The derivative of norbornene was synthesized as similar to that of the fourteenth example except that the present inventors used acrylate of the second example instead of the acrylate of the third example.

SIXTEENTH EXAMPLE

The present inventors synthesized polymer in norbornene series. The polymer contained a structural unit expressed by the general formula (4') at 50 mole % and another structural unit expressed by the general formula (4'a) at 50 mole %. The structural units were expressed by the following structural formulae.

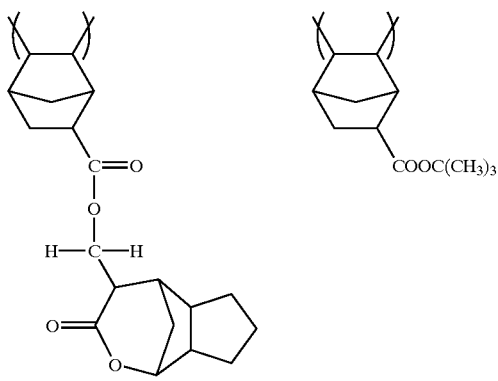

The first structural unit was expressed by the general formula (4') where $R^1$, $R^2$, $R^3$, $R^4$, $R^5$ and $R^6$ were hydrogen atoms, $R^7$ and $R^8$ were propylene groups, i.e., [—(CH$_2$)$_3$—] bonded to each other for forming a ring and n was 1. On the other hand, the second structural unit was expressed by the general formula (4'a) where $R^{13}$ was hydrogen atom and $R^{14}$ was t-butoxycarbonyl group.

The derivative of norbornene was synthesized as follows. 0.131 gram of di-$\mu$-chlorobis [($\eta$-allyl) palladium (II)] and 0.244 gram of hexafluorosilver antimonate were dissolved in 22 milliliters of chlorobenzene, and were agitated at room temperature. After 20 minutes, the reactant mixture was filtrated, and the filtrate was added to mixture containing 11.44 grams of the derivative of norbornene of the fourteenth example, 7.03 grams of 5-norbornene-2-carboxylic acid t-butyl ester, 0.1 milliliter of water and 85 milliliters of chlorobenzene. The solution was agitated for 20 hours at room temperature, and, thereafter, was added to 600 milliliters of methanol. Resin was precipitated, and was filtrated. The resin was dissolved in 75 milliliters of chlorobenzene, and 15 milliliters of methanol and 1.6 grams of sodium borohydride were added thereto. Agitation was continued for 3 hours at room temperature, and the solution was left as it was for 24 hours at room temperature. Pd (0) particles were precipitated. The particles were filtrated, and the filtrate was poured in 500 milliliters of methanol. Resin was precipitated, and was filtrated. Then, 8.86 grams of the objective resin was obtained. The yield was 48%. The weight average molecular weight Mw was 13000, and the degree of dispersion Mw/Mn was 2.36.

SEVENTEENTH EXAMPLE

The present inventors synthesized polymer in norbornene series which contained a structural unit expressed by the general formula (4') at 25 mole %, another structural unit expressed by the general formula (4'b) at 25 mole % and yet another structural unit expressed by the general formula (4'c) at 50 mole %. The structural units were expressed as follows.

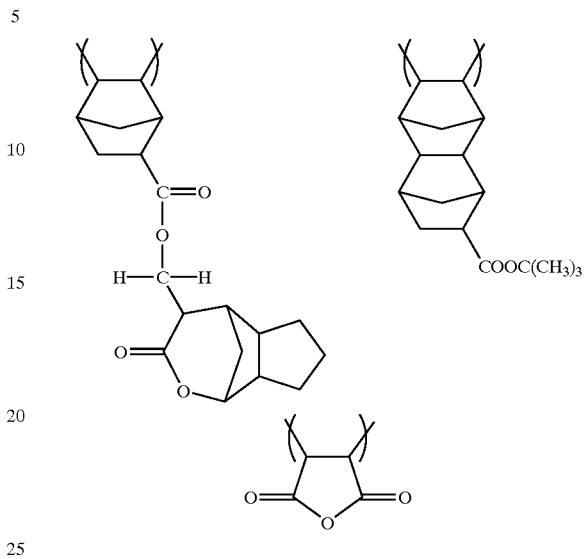

The first structural unit was expressed by the general formula (4') where $R^1$, $R^2$, $R^3$, $R^4$, $R^5$ and $R^6$ were hydrogen atoms, $R^7$ and $R^8$ were propylene groups, i.e., [—(CH$_2$)$_3$—] bonded to each other for forming a ring and n was 1. On the other hand, the second structural unit was expressed by the general formula (4'b) where $R^{15}$ was hydrogen atom and $R^{16}$ was t-butoxycarbonyl group.

The polymer was synthesized as follows. 2 grams of the derivative of norbornene of the fourteenth example, 1.646 grams of 3-tetracyclododecene-8-carboxylic acid t-butyl ester and 1.24 grams of maleic anhidride were dissolved in 10 milliliters of tetrahydrofuran in a 100 ml flask with a reflux tube. 41.5 milligrams of AIBN was added to the solution, and was agitated in argon atmosphere at 60 degrees to 65 degrees in centigrade. After 20 hours, the resultant solution was cooled, and the reactant mixture was poured into 100 milliliters of ether. The precipitate was filtrated, and was refined through the precipitation, again. Then, 1.5 grams of polymer was obtained. The yield was 31%.

The polymer was analyzed. The weight average molecular weight Mw was determined to be 5700 through GPC analysis, and the degree of dispersion Mw/Mn was 2.34.

EVALUATIONS

The present inventors evaluated the polymer and chemically amplified resist as follows.

RESISTANCE AGAINST ETCHING 2 grams of the polymer of the fourth example was dissolved in 10 grams of propyleneglycolmonoethylether acetate, and the solution was passed through a 0.2 micron Teflon filter. Subsequently, the filtrate was spun onto a 3-inch silicon wafer, and, thereafter, was baked on a hot plate at 90 degrees in centigrade for 60 seconds. A thin resist layer of 0.7 micron thick was formed on the silicon wafer. The silicon wafer was put into a chamber of a reactive ion etching system, which was manufactured and sold by Nichiden-Anerba Corporation as DEM451. CF$_4$ gas was supplied into the chamber, and dry etching was carried out on the conditions that the electric power was 100 watts, pressure was 5 Pa and gas flow was 30 sccm. After the dry etching, the resistance against the dry etching was evaluated on the basis of the etching speed.

The resistance against the dry etching was evaluated for the polymer of the ninth example and the polymer of the sixteenth example as similar to the polymer of the fourth example.

As comparative examples, novolak resist, poly (p-vinylphenol) and poly (methylmethacrylate) were evaluated as similar to the fourth, ninth and sixteenth examples. The poly (p-vinylphenol) was used as the basic resin for KrF resist. The novolak resist and the poly (p-vinylphenol) were sold in the market. The poly (methylmethacrylate) did not have any bridged cyclic hydrocarbon group in the molecular structure. The values of the etching speed were normalized with respect to that of the novolak resist as shown in the following table.

| Polymer | Etching Speed (Relative Ratio) |
| --- | --- |
| Example 4 | 1.2 |
| Example 9 | 1.15 |
| Example 16 | 1.15 |
| Poly (methylmethacrylate) | 1.9 |
| Poly (p-vinylphenol) | 1.2 |
| Novolak Resist (PFI-15A) | 1 |

The etching on the polymers according to the present invention was slower than that on the poly (p-vinylphenol). Thus, the polymers according to the present invention exhibited large resistance against the dry etching.

TRANSPARENCY 1.8 grams of the polymer of the fourth example was dissolved in 10 grams of propyleneglycolmonoethylether acetate, and the solution was filtrated through a 0.2 micron Teflon filter. Subsequently, the filtrate was spun onto a 3-inch quartz plate, and, thereafter, was baked on a hot plate at 90 degrees in centigrade for 60 seconds. A thin resist layer of 0.4 micron thick was formed on the quartz plate. Using an ultra-violet/visual range spectrophotometer, the. present inventors measured the transmittance to 193.4 nm wavelength ray, which was the central wavelength of ArF excimer laser light.

The transparency was also evaluated for the polymer in the acrylic series, i.e., the ninth example and the polymer in the norbornene series, i.e., the sixteenth example as similar to the polymer of the fourth example.

The transmittance of the fourth example was 83%/0.4 micron, the transmittance of the ninth example was 81%/0.4 micron, and the transmittance of the sixteenth example was 73%/0.4 micron. The present inventors concluded that the polymers according to the present invention exhibited transparency large enough to use it as a single layer resist.

PATTERN FORMING PROPERTY

The present inventors produced solution containing (1) 2 grams of polymer in acrylic series obtained as the fourth example, (2) 0.04 gram of triphenylsulfonium nonaflate serving as photo-acid generator, and (3) 11.5 grams of propyleneglycolmonoethylether acetate.

The present inventors filtrated the solution with a 0.2 micron Teflon filter, and produced a chemically amplified resist.

An 8-inch silicon wafer was coated with 0.1 micron organic anti-reflection layer, which was manufactured by Brewer Corporation as DUV-30J, and the chemically amplified resist was spun thereonto. The chemically amplified resist was baked on a hot plate at 110 degrees in centigrade for one minute. Then, the anti-reflection layer was overlaid by a chemically amplified resist layer of 0.4 micron thick.

The silicon wafer coated with the chemically amplified resist layer was put into an ArF reduction projection aligner, which was manufactured by Nikon Corporation. The numerical aperture was 0.6. The chemically amplified resist layer was exposed to ArF excimer laser light so as to form a latent image therein.

After the exposure to the light, the silicon wafer was baked on the hot plate at 130 degrees in centigrade for 60 seconds, and, thereafter, was dipped in 2.38% water solution of $(CH_3)_4$ NOH (TMAH) for 60 seconds. The latent image was developed. After the development, the chemically amplified resist layer was rinsed in pure water for 60 seconds, and a positive resist pattern was formed on the silicon wafer.

The present inventors similarly produced another sort of chemically amplified resist on the basis of the polymer in acrylic series produced as the ninth example and yet another sort of chemically amplified resist one the basis of the polymer in norbornene series produced as the sixteenth example. Using these sorts of chemically amplified resist, the positive pattern was transferred to the chemically amplified resist layers as similar to the above.

The present inventors evaluated those sorts of chemically amplified resist from the viewpoints of sensitivity and resolution. The evaluation was summarized in the following table.

| Chemically Amplified Resist Containing | Resolution ($\mu$mL/S) | Sensitivity (mJ/cm$^2$) |
| --- | --- | --- |
| Fourth example | 0.14 | 20.4 |
| Ninth example | 0.13 | 15.6 |
| Sixteenth example | 0.15 | 22.0 |

Thus, the present inventors concluded that the chemically amplified resist according to the present invention exhibited good pattern forming property.

ADHESION TO SUBSTRATES

The present inventors spread the chemically amplified resist according to the present invention on substrates, and observed the boundary between the chemically amplified resist layers and the substrates through a scanning electron microscopy. The chemically amplified resist layers were strongly adhered to the substrates, and did not peel off Thus, the present inventors concluded that the chemically amplified resist had good adhesion to substrates.

The present inventors evaluated other sorts of chemically amplified resist produced on the basis of other polymers in similar manners to those described hereinbefore. The results were summarized as follows.

The present inventors confirmed that chemically amplified resist produced on the basis of the polymer in acrylic series, i.e., each of the fifth to eighth and tenth to thirteenth examples exhibited large resistance against etching, high transparency, high sensitivity, good resolution and good adhesion to substrates.

The present inventors further confirmed that chemically amplified resist produced on the basis of the polymer in norbornene series, i.e., the seventeenth example exhibited large resistance against etching, high transparency, high sensitivity, good resolution and good adhesion to substrates. The present inventors further synthesized a derivative of (meth)acrylate expressed by the general formula (3) where n is zero. A derivative of 3-oxo-4-oxabicyclo[3.2.1]otane reacted with triphenylmethyllithium and, thereafter, with 1,2-dibromoethane to 2-bromo compound. The 2-bromo compound reacted with (meth)acrylic acid in the presence of basic catalyst. Then, the present inventors obtained (meth) acrylate expressed by the general formula (3) where n is zero. The derivative of (meth)acrylate reacted with cyclopentadiene. Then, a derivative of norbornene at n=zero was obtained. The monomers, i.e., the derivative of (meth) acrylate and the derivative of norbornene were vinyl polymerized to obtain polymer. Chemically amplified resist was produced on the basis of the polymer, and the present inventors evaluated the chemically amplified resist. The present inventors confirmed that the chemically amplified resist exhibited large resistance against etching, high transparency, high sensitivity, good resolution and good adhesion to substrates.

As will be appreciated from the foregoing description, the polymer and chemically amplified resist according to the present invention have the bridged alicylic δ lactone structure so that the large resistance against dry etching, high transparency, good resolution and good adhesion to substrates are achieve. Using the chemically amplified resist, the-manufacturer can transfer fine patterns to silicon wafers in the fabrication process of ultra large scale integration in the next generation Although particular embodiments of the present invention have been shown and described, it will be apparent to those skilled in the art that various changes and modifications may be made without departing from the spirit and scope of the present invention.

What is claimed is:

1. A photoresist comprising polymer comprising vinyl polymer having 3-oxo-4-oxabicyclo[3.2.1]octane-2-yl group expressed by general formula (1)

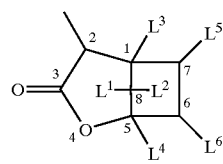

(1)

where each of $L^1$, $L^2$, $L^3$, $L^4$, $L^5$ and $L^6$ is selected from the group consisting of hydrogen atom and alkyl groups having the carbon number from 1 to 8, and photo-acid generator generating acid in the presence of light equal in wavelength to or less than 220 nanometers, the ratio of said photo-acid generator to said photoresist being fallen within the range from 0.2% by mass to 30% by mass.

2. The photoresist as set forth in claim 1, in which one of said hydrogen atom and said alkyl groups at $L^5$ and one of said hydrogen atom and said alkyl groups at said $L^6$ are replaced with alkylene groups having the carbon number from 1 to 10 and bonded to each other for forming a ring.

3. The photoresist as set forth in claim 1, in which said vinyl polymer comprises at least one structural unit polymerized with vinyl monomer selected from the group consisting of ethylene, derivatives of ethylene, vinyl chloride, derivatives of vinyl chloride, styrene, derivatives of styrene, acrylonitrile, derivatives of acrylonitrile, (meth)acrylate, derivatives of (meth)acrylate, norbornene carboxylic acid ester and derivatives of norbornene carboxylic acid ester.

4. The polymer as set forth in claim 3, in which the vinyl monomers in acrylic series have a bridged alicylic δ lactone structure expressed by general formula (3')

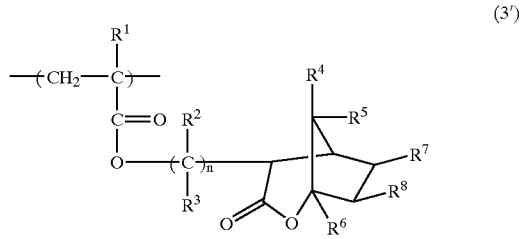

(3')

where $R^1$ is selected from the group consisting of hydrogen atom and methyl group, each of $R^2$ and $R^3$ is selected from the group consisting of hydrogen atom and alkyl groups having the carbon numbers from 1 to 4, each of $R^4$, $R^5$ and $R^6$ is selected from the group consisting of hydrogen atom and methyl group, $R^7$ and $R^8$ are hydrogen atoms or alkylene groups having the carbon number from 1 to 10 and bonded to each other for forming a ring and n is zero or 1.

5. The photoresist as set forth in claim 3, in which the vinyl polymers in norbornene series have a bridged alicylic δ lactone structure expressed by general formula (4')

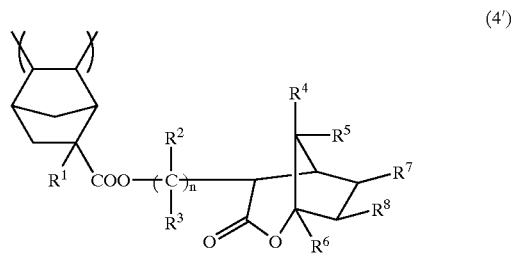

(4')

where $R^1$ is selected from the group consisting of hydrogen atom and methyl group, each of $R^2$ and $R^3$ is selected from the group consisting of hydrogen atom and alkyl groups having the carbon number from 1 to 4, each of $R^4$, $R^5$ and $R^6$ is selected from the group consisting of hydrogen atom and methyl group, $R^7$ and $R^8$ are hydrogen atoms or alkylene groups having the carbon number from 1 to 10 and bonded to each other for forming a ring and n is zero or 1.

6. A photoresist comprising polymer comprising vinyl polymer having a bridged alicylic δ lactone structure expressed by general formula (2)

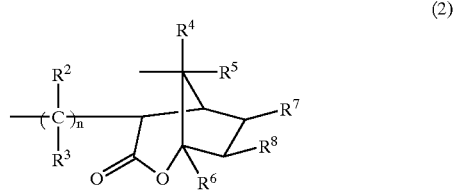

(2)

where each of $R^2$ and $R^3$ is selected from the group consisting of hydrogen and alkyl groups having the carbon number from 1 to 4, each of $R^4$, $R^5$ and $R^6$ is selected from the group consisting of hydrogen atom and methyl group, $R^7$ and $R^8$ are hydrogen atoms or alkylene groups each having the carbon number from 1 to 10 and bonded for forming a ring and n is zero or 1, and photo-acid generator generating acid in the presence of light equal in wavelength to or less than 220 nanometers, the ratio of said photo-acid generator to said photoresist being fallen within the range from 0.2% by mass to 30% by mass.

7. The photoresist as set forth in claim 6, in which said vinyl polymer comprises at least one structural unit polymerized with vinyl monomer selected from the group consisting of ethylene, derivatives of ethylene, vinyl chloride, derivatives of vinyl chloride, styrene, derivatives of styrene, acrylonitrile, derivatives of acrylonitrile, (meth)acrylate, derivatives of (meth)acrylate, norbornene carboxylic acid ester and derivatives of norbornene carboxylic acid ester.

8. The photoresist as set forth in claim 7, in which the vinyl polymers in acrylic series have a bridged alicylic δ lactone structure expressed by general formula (3')

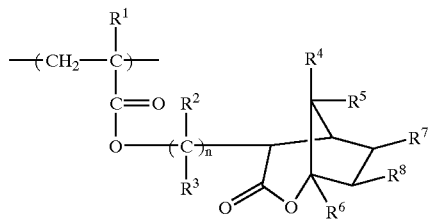

(3')

where $R^1$ is selected from the group consisting of hydrogen atom and methyl group, each of $R^2$ and $R^3$ is selected from the group consisting of hydrogen atom and alkyl groups having the carbon numbers from 1 to 4, each of $R^4$, $R^5$ and $R^6$ is selected from the group consisting of hydrogen atom and methyl group, $R^7$ and $R^8$ are hydrogen atoms or alkylene groups having the carbon number from 1 to 10 and bonded to each other for forming a ring and n is zero or 1.

9. The photoresist as set forth in claim 7, in which the vinyl polymers in norbornene series have a bridged alicylic δ lactone structure expressed by general formula (4')

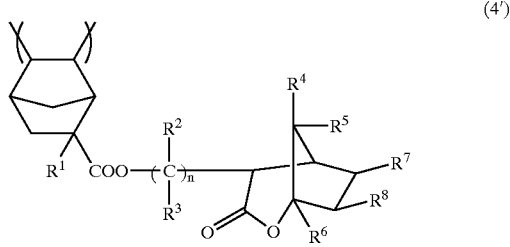

(4')

where $R^1$ is selected from the group consisting of hydrogen atom and methyl group, each of $R^2$ and $R^3$ is selected from the group consisting of hydrogen atom and alkyl groups having the carbon number from 1 to 4, each of $R^4$, $R^5$ and $R^6$ is selected from the group consisting of hydrogen atom and methyl group, $R^7$ and $R^8$ are hydrogen atoms or alkylene groups having the carbon number from 1 to 10 and bonded to each other for forming a ring and n is zero or 1.

* * * * *